United States Patent [19]

Commandeur et al.

[11] Patent Number: 5,202,514

[45] Date of Patent: Apr. 13, 1993

[54] DECHLORINATED BENZYLTOLUENE/DIBENZYLTOLUENE OLIGOMER DIELECTRIC LIQUIDS

[75] Inventors: Raymond Commandeur, Vizille; Daniel Missos, Grenoble, both of France

[73] Assignee: Atochem, Puteaux, France

[21] Appl. No.: 635,673

[22] Filed: Dec. 28, 1990

[30] Foreign Application Priority Data

Dec. 28, 1989 [FR] France ................. 89 17365

[51] Int. Cl.[5] .............................................. C07C 2/02
[52] U.S. Cl. ..................... 585/426; 585/422; 585/425; 585/446; 585/462; 585/469
[58] Field of Search ............... 585/422, 425, 426, 446, 585/462, 469

[56] References Cited

U.S. PATENT DOCUMENTS

| 4,197,417 | 4/1980 | Morley | 585/455 |
| 4,523,044 | 6/1985 | Commandeur et al. | 585/11 |
| 4,929,784 | 5/1990 | Klinkmann et al. | 585/422 |

*Primary Examiner*—Patrick P. Garvin
*Assistant Examiner*—E. D. Irzinski
*Attorney, Agent, or Firm*—Burns, Doane, Swecker & Mathis

[57] ABSTRACT

Benzyltoluene/dibenzyltoluene oligomers essentially devoid of contaminating amounts of chlorine values, well adapted as dielectric liquids, are prepared by (a) condensing benzyl chloride with toluene or with lower benzyltoluene oligomers in the presence of a catalytically effective amount of ferric chloride, and then (b) directly dechlorinating the crude product of condensation, e.g., by contacting same with sodium methylate.

8 Claims, No Drawings

DECHLORINATED BENZYLTOLUENE/DIBENZYLTOLUENE OLIGOMER DIELECTRIC LIQUIDS

BACKGROUND OF THE INVENTION

1. Field of the Invention

The present invention relates to the preparation or synthesis of benzyltoluene and dibenzyltoluene compositions of low chlorine content and to the use of such compositions as dielectric liquids.

2. Description of the Prior Art

Oligomer and polyarylalkane compositions useful as dielectric liquids have been described in European Patent EP 136,230. These compositions are based essentially on benzyltoluene and dibenzyltoluene and are prepared by chlorinating toluene to benzyl chloride and then condensing the benzyl chloride with the remaining toluene via a Friedel-Crafts reaction.

In the above process, as in any process entailing a Friedel-Crafts reaction, it is not always easy to completely remove the hydrochloric acid produced by the condensation of benzyl chloride with toluene. Moreover, the benzyl chloride can also contain chlorobenzyl chloride, $C_6H_4Cl$—$CH_2Cl$, which produces chlorobenzyltoluene, $C_6H_4Cl$—$CH_2$—$C_6H_4$—$CH_3$, by a Friedel-Crafts reaction.

A product (composition) which does not contain chlorine is desired for most dielectric applications. EP 306,398 describes a process for destroying organic products halogenated on the aryl carbon atoms; in particular, Example 1 illustrates the removal of the chlorobenzyltoluene present in dibenzyltoluene.

In the current state of this art, as soon as the Friedel-Crafts condensation reaction was complete, the catalyst was destroyed, for example, by washing with dilute hydrochloric acid, followed by washing with water up to the point of neutrality.

SUMMARY OF THE INVENTION

It has now unexpectedly been determined that when ferric chloride is used as a Friedel-Crafts catalyst in the above reaction, it is no longer necessary to perform a washing operation to remove it and that the dechlorination can be conducted on the crude condensation product.

Briefly, the present invention features a process for the synthesis of benzyltoluene oligomers in which benzyl chloride is condensed with toluene or with lower benzyltoluene oligomers in the presence of ferric chloride and then the chlorinated organic products are directly removed therefrom.

DETAILED DESCRIPTION OF THE PREFERRED EMBODIMENTS OF THE INVENTION

More particularly according to the present invention, the condensation of benzyl chloride with toluene is a reaction which is, per se, known to this art and which can be carried out in the presence of any Friedel-Crafts catalyst, in particular, in the presence of ferric chloride.

By the term "benzyltoluene oligomers" is intended a mixture of isomers having the formula A:

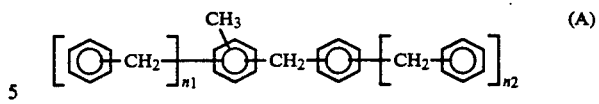

in which $n_1$ and $n_2$ have the value 0, 1 or 2 and $n_1+n_2$ is less than or equal to 3.

By "benzyltoluene" are intended oligomers in which $n_1+n_2=0$ and by "dibenzyltoluene" are intended the oligomers in which $n_1+n_2=1$.

The lower benzyltoluene oligomers are similar to the benzyltoluene oligomers but contain fewer benzyl recurring units. For example, benzyltoluene ($n_1+n_2=0$) is a lower benzyltoluene oligomer in comparison with dibenzyltoluene ($n_1+n_2=1$). When, for example, benzyltoluene ($n_1+n_2=0$) is condensed with benzyl chloride, at least some dibenzyltoluene ($n_1+n_2=1$) can be obtained.

It would also be within the scope of the invention if the condensation of benzyl chloride were to be carried out using a mixture of toluene and of lower dibenzyltoluene oligomers.

In practice, the condensation is carried out at a temperature ranging from 50° to 150° C. The amount of ferric chloride advantageously ranges from 50 ppm to 1% by weight of the reaction mass.

The reaction mixture thus obtained and which consists essentially of benzyltoluene oligomers and of a possible excess of toluene may contain chlorinated organic compounds such as chlorotoluenes, chlorobenzyltoluene and, in general, benzyltoluene oligomers bearing one or more chlorine atoms on the benzene nuclei. These compounds have been introduced or are formed from impurities in the benzyl chloride or by ferric chloride.

Such reaction mixture is directly treated to remove the chlorinated organic compounds therefrom, i.e., without requiring the removal of the condensation catalyst, ferric chloride.

Any technique can be employed for destroying the chlorinated organic compounds, for example, the process described in EP 306,398, using an alkali metal alcoholate; the process described in EP 225,849, using sodium metal; and the process described in EP 250,748, using a heavy alcoholate. It is preferred to utilize the dechlorination process described in EP 306,398.

In a preferred embodiment of the invention, the reaction mixture obtained when the condensation reaction is finished is contacted with an alcoholate and the entire mass is heated with stirring to a temperature ranging from 220° to 320° C. It is advantageous that the excess toluene which may be present in the reaction mixture be removed by distillation between completion of the condensation of benzyl chloride and the dechlorination. This toluene can be recycled upstream.

After the dechlorination treatment, a single distillation is sufficient to recover the benzyltoluene oligomers of low chlorine content. A heavy fraction containing the residues of the dechlorinating agent, NaCl, iron salts and heavy benzyltoluene oligomers remains as distillation bottoms.

It is also within the scope of the invention to recycle this heavy fraction, partly or completely, for use either by itself or mixed with the reagent used to destroy the chlorinated organic compounds.

It is likewise within the scope of the invention to recycle the benzyltoluene, either wholly or partially, to the condensation stage, after the condensation and before the dechlorination. The toluene and the benzyltoluene can then be removed from the reaction mixture, it being possible for the toluene to be recycled upstream to produce benzyl chloride, or merely recycled to the condensation.

One advantage of recycling the benzyltoluene, either partially or completely, is that it increases the proportion of dibenzyltoluene in the oligomers.

The benzyl chloride may also contain benzylidene chloride; ditolylphenylmethane oligomers are then obtained mixed with the benzyltoluene oligomers, the former oligomers being a mixture of isomers of formula B:

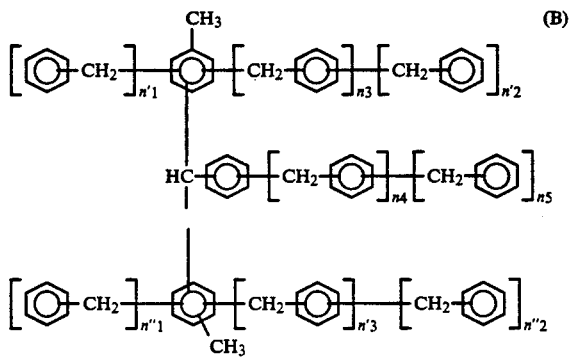

in which $n'_1$, $n''_1$ and $n_4$ have the value 0, 1 or 2; $n'_2$, $n''_2$, $n_3$, $n'_3$ and $n_5$ have the value 0 or 1; and with the proviso that $n'_1+n''_1+n'_2+n''_2+n_3+n'_3+n_4+n_5$, represented by $S_n$, is less than or equal to 2.

It too is within the scope of the invention to first chlorinate toluene and then to conduct the condensation in the presence of ferric chloride directly on this mixture. After such chlorination, a distillation may be carried out, if desired, to separate benzylidene chloride therefrom.

It will, of course, be appreciated that the process described can be carried out continuously or discontinuously.

The oligomers produced are useful dielectric liquids.

To permit these oligomers to be better employed as dielectrics, it is advantageous to purify them by a technique employing a fuller's earth or activated alumina, either by themselves or mixed, such techniques being, per se, known to the art of dielectric liquids.

Similarly, it may be advantageous to add stabilizers of the epoxide type or of another type, such as, for example, tetraphenyltin or anthraquinone-based compounds which are typically employed in such applications.

These adjuvants are generally hydrochloric acid scavengers and are added in amounts which advantageously range from 0.001% to 10%, preferably from 0.01% to 0.3%.

In order to further illustrate the present invention and the advantages thereof, the following specific examples are given, it being understood that same are intended only as illustrative and in nowise limitative.

EXAMPLE 1

3 moles of toluene and 60 mg of ferric chloride were introduced into a reactor fitted with a stirrer, a condenser and a nitrogen injector. The entire assembly was heated to 100° C. and 1 mole of benzyl chloride was introduced, over 1 hour. The reaction mass was maintained stirred for another 1 hour at 100° C. The excess toluene was removed by vacuum distillation. The residue, essentially consisting of benzyltoluene oligomers of type (A), was treated with 1% of sodium methylate for 6 hours at 290° C. under a nitroqen blanket. The mixture was then subjected to flash evaporation at 300° C. at 2 mm of mercury and a distillate was produced that was a mixture of oligomers of type (A) having the following composition by weight:

| | |
|---|---|
| $n_1 + n_2 = 0$ | 66% |
| $n_1 + n_2 = 1$ | 24% |
| $n_1 + n_2 = 2$ | 10%. |

The chlorine content was less than 5 ppm.

EXAMPLE 2

The procedure of Example 1 was repeated, using the unreacted toluene from this operation and replenishing same with fresh toluene.

The mixture of oligomers of type A obtained after distillation had a chlorine content which was less than 5 ppm.

EXAMPLE 3

31.5 moles of benzyltoluene and 3.5 g of ferric chloride were charged into a reactor fitted with a stirrer and a condenser. The temperature was increased to 130° C. and 6.3 moles of benzyl chloride were introduced, over 4 hours. The reaction mixture was then maintained at 130° C. for another hour.

The mixture was then treated with 50 g of sodium methylate for 3 hours at 290° C.

The reaction mass was then subjected to vacuum distillation at 0.5 mm of mercury using a packed column filled with glass rings (4 plates). The first fraction, distilling at about 100° C., contained unreacted benzyltoluene (4,000 g). The following fraction (1,000 g), distilling between 180° and 185° C., had a purity of 98% as dibenzyltoluene, namely, as oligomer (A) in which $n_1+n_2=1$.

The chlorine content was less than 5 ppm.

EXAMPLE 4

4 moles of toluene were introduced into a reactor fitted with a stirrer, a condenser, a chlorine feed tube and a 30-watt Philips TLADK lamp. 1 mole of gaseous chlorine was then introduced while the temperature was maintained at 80° C. for 1 hour. This mixture was then placed in a dropping funnel and was introduced, over 2 hours, into a reactor fitted with a stirrer and containing 2 moles of toluene with 100 mg of ferric chloride at 100° C. The reaction mixture was maintained stirred at 100° C. for another 2 hours.

The excess toluene was removed by vacuum distillation.

The residue, consisting essentially of benzyltoluene oligomers (A) and of oligomers derived from ditolylphenylmethane (B) was treated with 2% of sodium methylate for 6 hours at 290° C. under a nitrogen blanket.

The mixture was then subjected to flash evaporation at 300° C. at 2 mm of mercury and produced a distillate essentially consisting of a mixture of the following compounds:

| | | |
|---|---|---|
| TYPE A | $n_1 + n_2 = 0$ | 78% |

-continued

|  | $n_1 + n_2 = 1$ | 15.5% |
|---|---|---|
|  | $n_1 + n_2 = 2$ | 4% |
| TYPE B: | $Sn = 0$ | 2% |
|  | $Sn = 1$ | 0.5% |

The chlorine content was less than 5 ppm.

EXAMPLE 5

The procedure of Example 4 was repeated using the unreacted toluene from this operation and replenishing same with fresh toluene.

The mixture of oligomers of type (A) and (B) obtained after distillation had a chlorine content which was less than 5 ppm.

EXAMPLE 6

A test identical with that described in the procedure of Example 1 was repeated. The crude mixture of oligomers obtained after separation of the unreacted toluene was treated for 6 hours at 290° C. in the presence of the distillation residue from Example 1, under a nitrogen blanket.

The mass was then subjected to a distillation at 300° C. at 2 mm of mercury.

The distillate essentially consisted of a mixture of oligomers of type (A) which had a chlorine content of less than 5 ppm.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of benzyltoluene oligomers essentially devoid of contaminating amounts of chlorine values, comprising (a) condensing benzyl chloride with toluene or with lower benzyltoluene oligomers in the presence of a catalytically effective amount of ferric chloride, and then (b) directly dechlorinating the crude product of condensation without first performing a washing operation to remove said ferric chloride.

2. The process as defined by claim 1, said dechlorination comprising directly reacting the crude product of condensation with sodium or an alkali metal alcoholate.

3. The process as defined by claim 2, said dechlorination comprising directly reacting the crude product of condensation with sodium methylate.

4. The process as defined by claim 1, comprising removing any excess toluene prior to the dechlorination step (b).

5. The process as defined by claim 1, comprising recycling at least a fraction of any benzyltoluene present to said condensation step (a), prior to said deohlorination step (b).

6. The process as defined by claim 1, comprising distilling the dechlorinated benzyltoluene oligomers and recycling distilland therefrom to said dechlorination step (b).

7. The process as defined by claim 1, carried out continuously.

8. The process as defined by claim 1, carried out discontinuously.

* * * * *